United States Patent [19]

Barnes et al.

[11] Patent Number: 4,954,251

[45] Date of Patent: Sep. 4, 1990

[54] CONCENTRIC MICROAGGREGATE BLOOD FILTER

[75] Inventors: Bruce E. Barnes, Kensington; Richard Furuzawa, Berkeley; Paul Kahn, San Francisco, all of Calif.

[73] Assignee: Miles Inc., Elkhart, Ind.

[21] Appl. No.: 304,735

[22] Filed: Jan. 31, 1989

[51] Int. Cl.[5] .................... B01D 29/35; B01D 29/58
[52] U.S. Cl. .................................... 210/806; 210/94; 210/323.2; 210/338; 210/436; 210/448; 210/489; 210/492; 210/767; 604/4; 604/406
[58] Field of Search .............. 210/435, 446, 436, 489, 210/492, 651, 767, 806, 323.1, 323.2, 335, 337, 338, 448, 94; 604/406, 4, 5

[56] References Cited

U.S. PATENT DOCUMENTS

| | | | |
|---|---|---|---|
| 3,506,130 | 4/1970 | Shaye | 210/446 |
| 3,557,786 | 1/1971 | Barr et al. | 210/446 |
| 3,593,854 | 12/1969 | Swank | 210/446 |
| 3,664,339 | 5/1972 | Santomieri | 210/446 |
| 3,765,536 | 10/1973 | Rosenberg | 210/449 |
| 3,935,111 | 1/1976 | Bentley | 210/446 |
| 4,035,304 | 7/1977 | Watanabe | 210/446 |
| 4,087,363 | 5/1978 | Rosemeyer et al. | 210/489 |
| 4,157,967 | 6/1979 | Meyst et al. | 210/449 |
| 4,450,078 | 5/1984 | Walker et al. | 210/448 |

FOREIGN PATENT DOCUMENTS 0024601  3/1981  European Pat. Off. ............ 210/338

OTHER PUBLICATIONS

Abstract P 5-02, W. H. Walker et al., A Simple Transfusion Device for Filtration of Blood with a 40 um Filter Screen, Proceedings of the International Society of Blood Transfusion, p. 144, 1984.

Primary Examiner—W. Gary Jones
Attorney, Agent, or Firm—James A. Giblin

[57] ABSTRACT

Microaggregate blood filter adapted to pre-filter aggregates larger than 150 microns without interfering with the on-going and continuous filtration of aggregates between 40 and 150 microns. Filter comprises a flexible housing having inlet and outlet ports and an interior nest of two generally cylindrical concentric outer and inner filter screens with a space between the screens. Blood to be filtered enters the housing from the top and is pre-filtered for aggregates larger than 150 microns by the inner screen. The inner screen defines a relatively large interior volume which allows filtered aggregates to collect by sedimentation at its lower portions in a manner that permits on-going, continuous, and unobstructed filtration of the blood through its upper portion for subsequent and final filtration through the outer 40 micron filter. A preferred filter has a transparent housing and built in drip chamber and can be primed without inverting the filter.

12 Claims, 4 Drawing Sheets

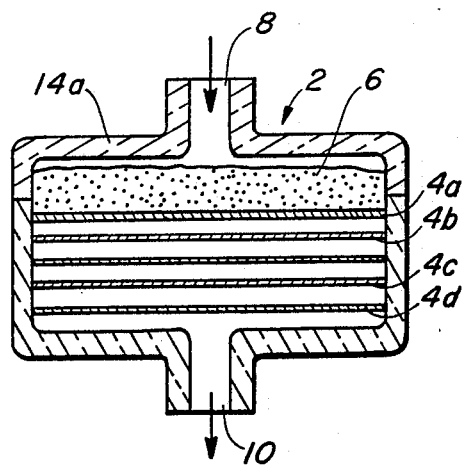
FIG._1.
(PRIOR ART)
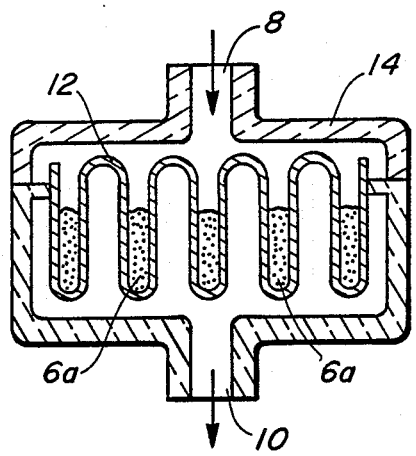
FIG._2.
(PRIOR ART)
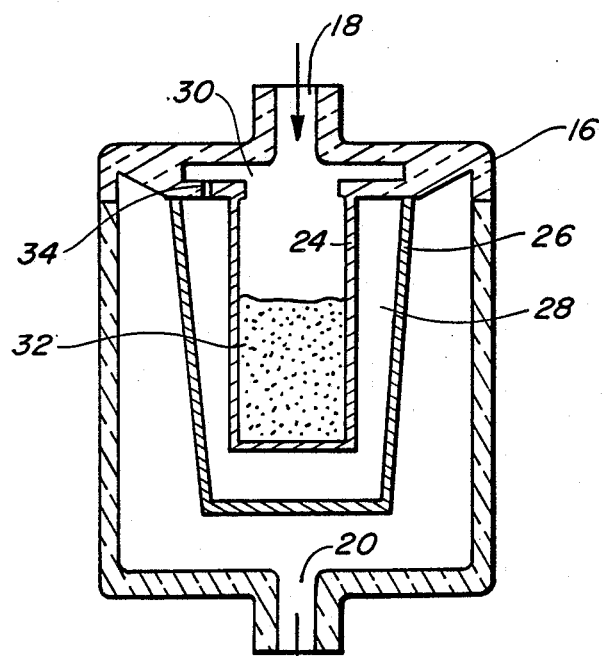
FIG._3.

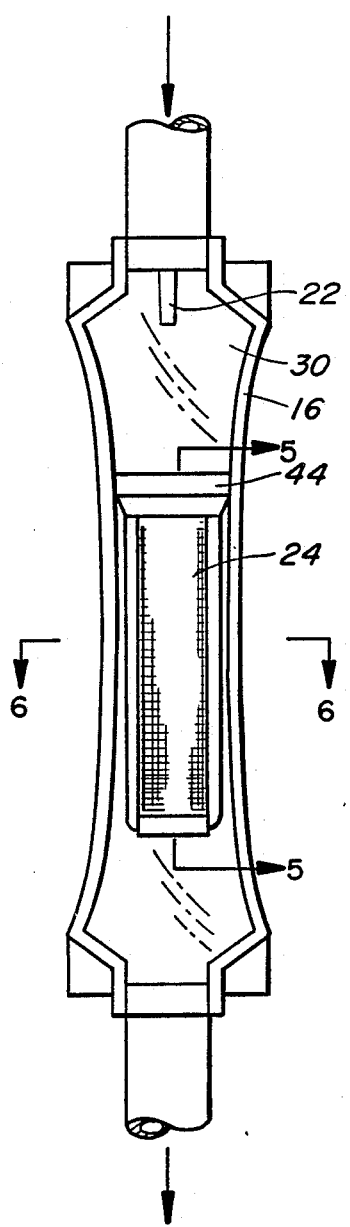 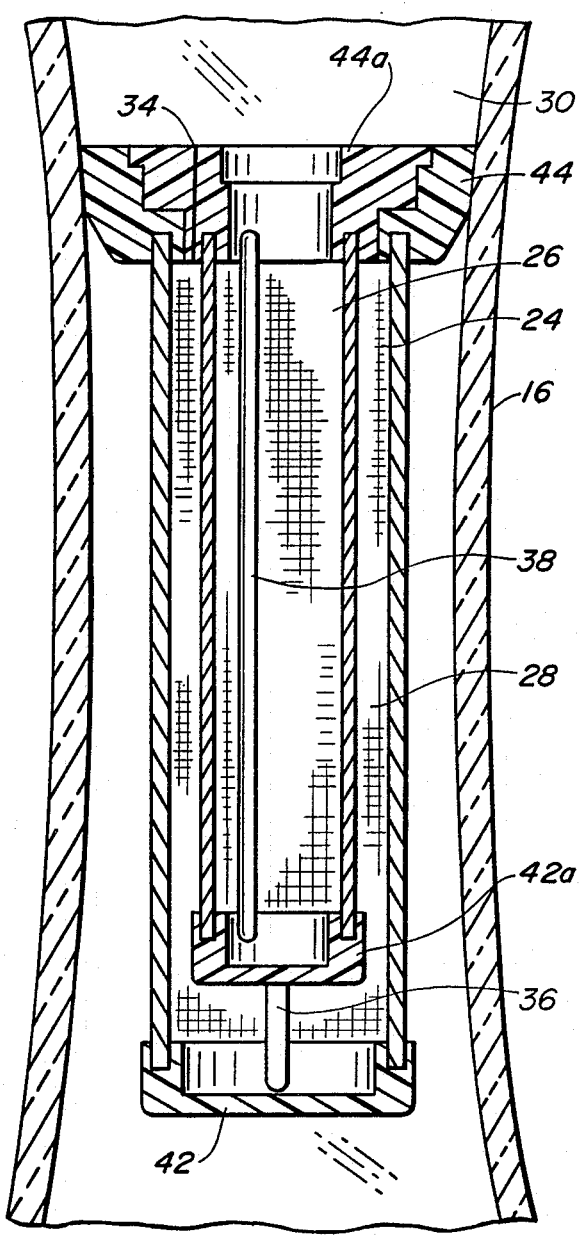
FIG._4.    FIG._5.

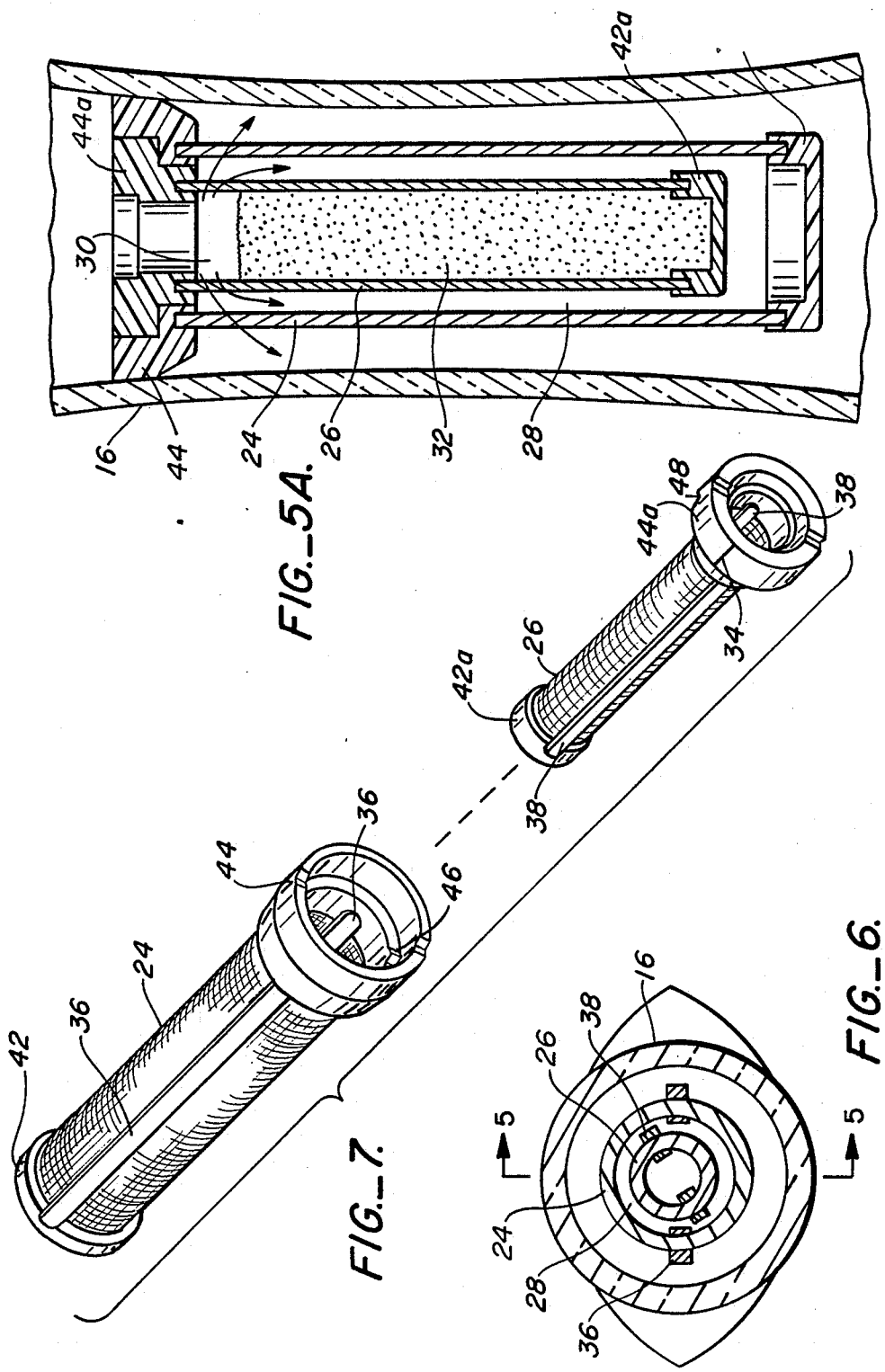

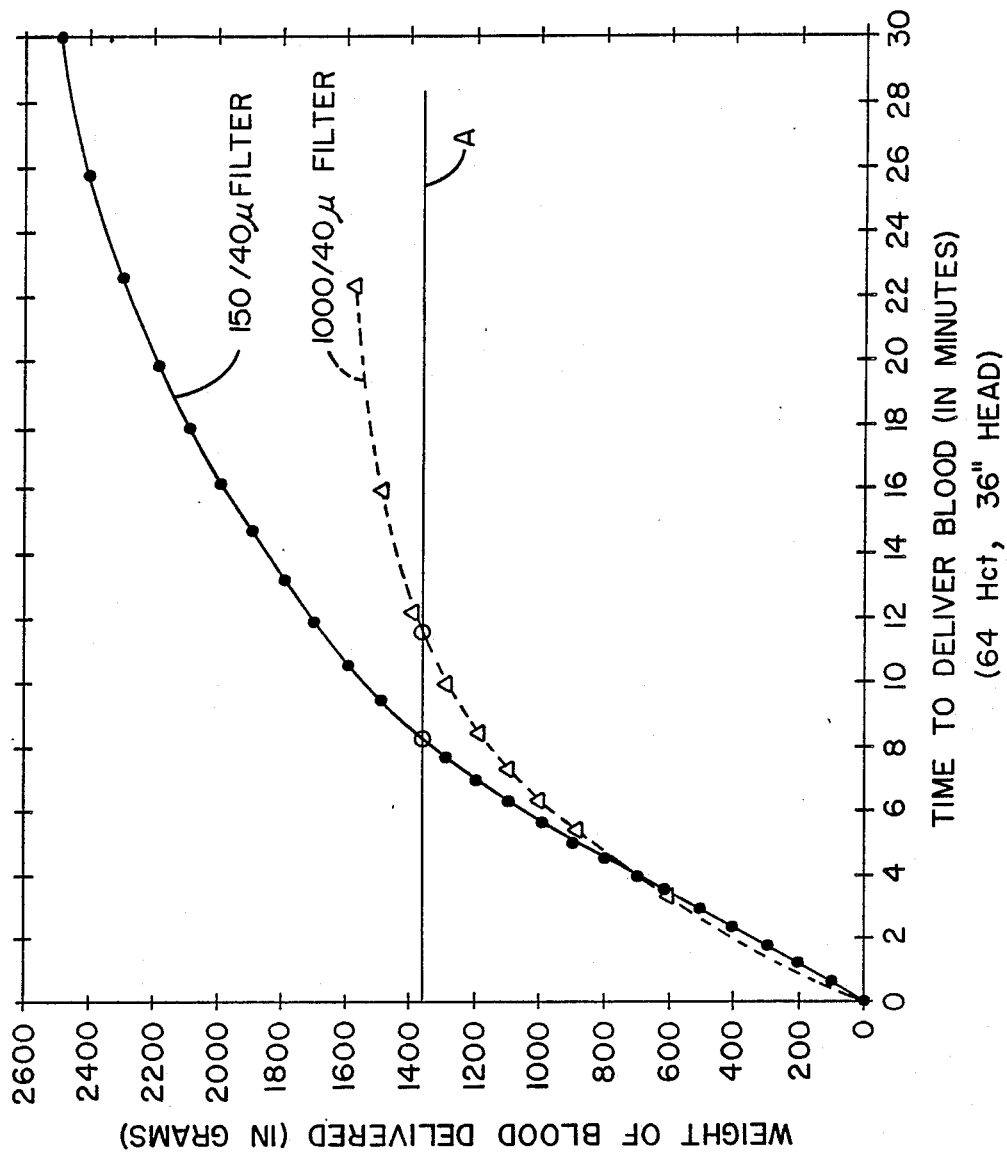
FIG._8.

CONCENTRIC MICROAGGREGATE BLOOD FILTER

BACKGROUND OF THE INVENTION

1. Field

This disclosure is concerned generally with filters and specifically with filters for human blood.

2. Prior art

When human red blood cells (RBC's) are transfused to a patient, they are first routinely passed through a filter known as a blood filter (or RBC filter) to remove blood clots or aggregates larger than a given size, usually expressed in microns. The majority of blood filters in use today are designed to filter out all clots and aggregates larger than about 210, 150 or 80 microns. These can be referred to as macroaggregate filters. However, there is a growing need and desire to filter out aggregates larger than about 40 microns. The filters that are capable of filtering out 40 micron and larger aggregates are commonly referred to as microaggregate filters. The present disclosure is concerned with an improved microaggregate filter (i.e. a blood filter capable of filtering clots and aggregates larger than about 40 microns from one or, preferably more, units of blood or red blood cells, prior to administration to a patient).

Present microaggregate filters are available in a variety of designs. Such filters may use either multiple layers of filter media or a relatively large area ($>135$ square centimeter) of a single filter of about 20 to 40 micron pore size. The latter design is commonly folded in accordion-like fashion to reduce the product to a size more convenient to use and store. In at least one such filter, the accordion pleats are separated by a relatively large mesh separation screen (1,000 micron pore size) which does not act as a filter medium. Microaggregate filters having such designs are described below and illustrated in the first two figures under the heading, prior art as FIGS. 1 and 2.

The above prior art designs are often unsatisfactory, especially for use in filtering more than a single unit of RBC's. Filters similar to that illustrated by FIG. 1, while effective for small quantities of blood, tend to become blocked by accumulated microaggregates and gelatinous clots, thereby forming occlusions at the filter surface of initial contact by the blood. The relatively small filtering surface area contributes to this problem. The filters of FIG. 2, while attempting to increase the filtering surface area per unit volume with pleats, tend to quickly occlude because the narrow pleat openings (typically about 1 mm) and shallow channels (typically about 1.5 cm) fill with clots, thereby rendering the larger surface area relatively useless. The large mesh (1,000 micron) screen separating the pleats is not designed to retain clots or aggregates of the type described in this disclosure.

A relatively recent attempt to avoid the above problems has been described in an Abstract at page 144 of the 1984 Proceedings of the International Society of Blood Transfusion. The Abstract by W. H. Walker et al. is entitled, "A Simple Transfusion Device for Filtration of Blood with a 40 μm Filter Screen." The filtration system consists of two filter screens with 150 and 40 micron mesh sizes and filter surface-areas of 23 and 36.5 $cm^2$, respectively. The device is described as having a priming volume of 35 ml and is said to be useful for both gravity and pressure transfusion. Experiments were said to show that 500 ml of CPD whole blood stored three weeks could be filtered by gravity flow within 2-3 minutes with a unit of packed CPD RBC's taking 3-4 minutes. Although the Abstract does not describe further filter structure details, the filter appears to have a relatively small volume to surface area ratio, thus raising questions as to whether, with time or with multiple units of blood being filtered, the accumulation of larger ($>150$ micron) clots and aggregates will permit an unimpeded flow of blood through the smaller micron (40) screen.

After considering the advantages and disadvantages of existing microaggregate filters, we have devised a significantly improved microaggregate filter which addresses the problems of flow obstruction associated with existing microaggregate filters. Details of our new filter are described below.

SUMMARY OF THE INVENTION

Our microaggregate blood filtering system comprises a flexible filter housing and is squeezable, to permit priming of the filter while remaining upright. The housing has upper inlet and lower outlet ports. The housing interior contains two generally cylindrical, elongated, concentric filtering screens. One screen is an inner pre-filter screen having a "mesh" or pore size capable of holding back clots and aggregates larger than about 150 microns and collecting them by sedimentation without substantially interfering with the continuous passage of smaller aggregates and red blood cells through the inner pre-filter and to the outer filter, spaced slightly away (preferably about 0.3 cm-0.6 cm) from the inner filter. The outer filter is capable of holding back clots and aggregates larger than about 40 microns. The elongated and cylindrical nature and relatively large volumes defined by the concentric screens permit clots and aggregates to fall by sedimentation to a lower volume portion of the filters, thereby minimizing adverse effects on the overall flow rate (or filtration) that would be otherwise caused by holding back or the retention of clots and aggregates by the respective screens.

This is particularly important for the inner pre-filter screen which is the first one through which the blood must pass. That screen should define a volume large enough (i.e. $>20$ $cm^3$) to collect by sedimentation the initially filtered clots $>150$ microns in a lower volume portion separate from the upper volume portion that permits the continuous, unobstructed flow of all blood having aggregates $<150$ microns. In other words, by using the filter in a vertical position with the inlet port on top, the pre-filtered larger clots, by sedimenting, will leave the upper surface area of the inner screen relatively open for the continuous, cascade-like overall flow and filtration. This same principle applies, but to a lesser extent, to the outer 40 micron screen, provided it is spaced at least about 0.3 cm away from the inner screen.

In a preferred embodiment, the filter includes an upper built-in visible drip tube and visible drip chamber occupying a portion of the volume just above the inner pre-filter. The flexible housing is transparent to permit observation of priming and drip and has controlled filtering surface areas and volumes to provide a critical factor value (described below) ranging from about 1.2 to about 1.5, preferably about 1.34. In the preferred filter of this disclosure there is also a space between the inner cylindrical housing walls and the outer surface of the outer filter screen averaging about 0.3 cm to assist in priming and to assure unimpeded flow of filtered blood or RBC's through the outer 40 micron filter and out the outlet to the patient. To assist in removing air from the above-described space, there is at least one small passage way (~1 mm) between the space between the screens and the inlet port (or the drip chamber). Our filtering system also permits the infusion of at least about five units of red blood cells into a patient using the same filter.

BRIEF DESCRIPTION OF THE FIGURES

FIGS. 1 and 2 are cross sectional illustrations of prior art microaggregate filters.

FIG. 3 is a cross sectional illustration of a commercially available filter illustrating certain features of both an earlier 210/80 macroaggregate (cf. microaggragate) filter and the microaggregate filter of this disclosure.

FIG. 4 shows a plan view of a preferred filter.

FIG. 5 shows a longitudinal cross sectional view taken at lines 5—5 of FIG. 4.

FIG. 5a shows a cross sectional view of the filter of FIG. 4 showing the flow direction of filtered blood.

FIG. 6 shows a cross sectional view taken at lines 6—6 of FIG. 4.

FIG. 7 shows an exploded view of the two generally cylindrical, elongated concentric filtering screens of the preferred filter of this disclosure.

FIG. 8 is a graph comparing time vs. volume of filtration using our filter and a prior art filter.

SPECIFIC EMBODIMENTS

The reasons for the detailed structure of our filter are based on a consideration of the volumes defined by the two filter screens, especially the volume defined by the inner screen, vis-a-vis mesh size ratio of the screens. As used herein, the terms "mesh", "mesh size", or their equivalent, refers to the size of the openings or pores in the so-called filter "screens", rather than the strict meaning of mesh (i.e. numbers of openings per inch). Thus, as used herein, mesh, mesh size, pore or pore size simply refer to the average size of the actual openings in microns ($\mu$) preferably uniform and uniformly distributed in a given filter screen that will just hold back clots or aggregates of a given size (i.e. a 40 mesh or 40 pore screen will hold back clots or aggregates >40 microns, etc).

The rational for our controlled mesh size and volumes is described below.

Volume/Area Ratio

Our invention is effective mainly because of the ratio of the elongated, inner filter volume to the area of the outer filter. In our preferred case, with 20 cm$^3$ inner filter volume, we found we could retain clots to allow passage of pre-filtered blood through the 56 cm$^2$ outer filter. This ratio $$\frac{\text{Inner Volume } V_I}{\text{Outer Area } A_o} = \frac{20}{56} = 0.357$$

The inner filter volume must be sufficiently large to contain the sedimented clots without occluding the inner screen. The outer area must be sufficiently large to allow passage of the filtered blood.

Mesh Size Ratio

The ratio of inner filter mesh size to outer mesh size is also important. Our 150$\mu$ inner pre-filter, combined with 40$\mu$ outer filter, yields the optimum combination of clot retention and filtered blood flow for a microaggregate filter. Experiments with other combinations (80$\mu$ inner/40$\mu$ outer) gave inferior results (see data below). The filter mesh ratio of $$\frac{150\mu}{40\mu} = 3.75$$

gave optimum results.

Critical Factor

Finally, the combination of these factors of Inner volume and Outer Area and Inner and Outer mesh sizes also describes a feature of our invention.

| | |
|---|---|
| Volume/Area Ratio = 0.357 | Mesh Size Ratio = 3.75 |
| Volume/Area Ratio × Mesh Size Ratio = Critical Factor 1.34 | |

Varying significantly from this ideal number would result in inadequate clot retentive volume, or inferior microaggregate filtration, or inadequate flow rate.

Ideal

Ideal
$$\frac{V_I \, 20}{A_o \, 56} \times \frac{M_I \, 150}{M_o \, 40} = 1.34$$

Inferior
$$\frac{V_I \, 20}{A_o \, 56} \times M_o \frac{M_I \, 80}{M_o \, 40} = 0.71 \text{ yields lower flow rate}$$

$$\frac{V_I \, 5.1}{A_o \, 135} \times \frac{M_I \, 1000}{M_o \, 40} = 0.94 \text{ clogs filter with clots, gives lower flow rate}$$

Thus, a preferred critical factor ranges from about 1.2 to about 1.5 as is very preferably 1.34.

Comparative Tests

Comparative tests were conducted to evaluate both dual screen 80/40 micron and 150/40 micron high flow blood filters with a commercially available microaggregate blood filter (Pall SQ40S). The objective was to determine comparative flow rates and volume throughout of the three filters and to determine the best microaggregate filter. Additionally, tests were conducted to determine microaggregate counts and % hemolysis. These additional tests showed removal of greater than 90% of aggregates of 40 microns and above with no significant increase in hemolysis.

The comparative tests were conducted using outdated RBC's (average of outdate was +9 days). Nineteen units of type matched RBC's were pooled and 800 ml of normal saline added to obtain a starting hematocrit of 61.

TABLE

| Test Results | Microaggregate Filters, Mesh Sizes | | |
|---|---|---|---|
| | 80/40 | 150/40 | 1000/40 |
| Total volume filtered (mls) | 1150 | 1700 | 1175 |
| Starting flow rate (ml/min) | 45.0 | 44.0 | 50.0 |
| Flow rate after 1st 500 mls | 62.5 | 72.5 | 65.0 |
| Flow rate after 2nd 500 mls | 12.5 | 74.0 | 11.5 |
| Flow rate at end of exp. | 4.0 | 8.5 | 2.0 |
| Time to filter 1st 500 mls | 11:12 | 11:25 | 10:13 |

TABLE-continued

| Test Results | Microaggregate Filters, Mesh Sizes | | |
|---|---|---|---|
| | 80/40 | 150/40 | 1000/40 |
| (avg flow rate for 500 mls) (ml/min) | (44.6) | (43.8) | (48.9) |
| Time to filter 2nd 500 mls | 23:10 (21.6) | 9:02 (55.4) | 18:45 (26.7) |
| Time to filter 3rd 500 mls | (1) | 17:15 (29.0) | (2) |
| | | (3) | |

(1) only 150 mls filtered in 45 minutes before experiment stopped (average flow 3.3 ml/min)
(2) 175 mls filtered in 45 minutes before experiment stopped (average flow 3.9 ml/min)
(3) additional 200 mls filtered in 25 minutes before experiment stopped (average flow 8.0 ml/min.)

The 150/40 micron high flow blood filter has a higher flow rate and larger throughput volume than the 80/40 micron or the commercially available 1000/40 micron blood filter. Using the same starting pool material, the 150/40μ filtered 500 mls more than the other two tested filters. The 150 micron filter takes out the larger particles and allows the 40 micron filter to screen out the 40-150 micron sized particles without reducing the flow or plugging the filters for a longer period of time.

The other two filters plug up faster because the 80/40 screens more particles in the 80 micron filter (80 microns +), the filter quickly plugs and flow drops. The commercial 1000/40 filter has a coarse screen before the 40 micron screen, but it acts primarily as a spacer and the 40 micron filter plugs as soon as all the internal volume area is filled up. Initially, the 1000/40 micron was flowing about 5 ml/min faster than the 150/40 during the first 500 mls, but during the second 500 mls the filter decreased in flow to 27 ml/min and the 150/40 increased to 55 ml/min. The 150/40 continued to filter a third 500 mls of blood at a flow rate of 29 ml/min, while the 1000/40 micron could filter only an additional 175 mls of blood before reaching a failure rate of 2 ml/min. The 150/40 continued to filter an additional 200 mls before the experiment was terminated. The 80/40 has flow rates slower than the 1000/40 micron and filtered approximately the same volume.

In further tests, the 150/40 filter delivered 2500 grams (2350 ml) of 64 Hct blood in 30 minutes with a final flow rate of 21 ml/min. In contrast, the commercially available 40 micron filter delivered 1600 grams (1505 ml) in 22 minutes. The final flow rate of that filter rapidly declined to less than 15 ml/min. Both filters were run at a 36" gravity head. Data of the above further tests and comparison are illustrated in FIG. 8. Line A of FIG. 8 represents the volume of about 4 units of red cells (one unit of blood equals approximately 325 ml of RBCs). As can be seen in FIG. 8, the 150/40 filter of this disclosure took only 8 minutes to filter about 4 units of RBCs (vs. 11 minutes for the 1000/40 filter).

DETAILED DESCRIPTION OF THE FIGURES

The illustrative prior art FIGS. 1 and 2 show how blood clots and aggregates can accumulate early in the filtration to occlude a large portion of the effective filtering surface area of both the multi-layered (FIG. 1) and pleated (FIG. 2) microaggregate filters. Where possible, the same numbers refer to similar parts in all Figures.

Some of the major advantages of our filter can be seen in the illustrated flow of blood and collection of clots and aggregates shown in FIG. 3.

FIGS. 1 and 2 illustrate how prior art microaggregate filters tend to clog, especially when used for multiple units of blood or even for a single unit of blood that, for various reasons, might have a relatively high amount of filterable clots or aggregates larger than microaggregates (i.e. greater in size than 40 microns).

FIG. 1 is an illustrative cross section of a filter 2 having multiple layers of filter media 4a, 4b, 4c and 4d having decreasing mesh sizes from top 4a to bottom 4d (which has the smallest mesh size such that only matter less than about 20-40 microns passes downwardly through the filter). As blood flows through the filter in the direction of the arrows, clots and larger aggregates 6 tend to accumulate in a random distribution over the entire top surface area of the top most filter layer which comes in first contact with the blood arriving from the upper inlet port 8. Depending on the volume (or units) of blood passed through inlet 8 and the sizes of aggregates it contains, it can be appreciated that the filter layers downward from filter layer 4a will see a progressively lesser volume of blood per unit of time.

FIG. 2 like FIG. 1, has inlet port 8 and outlet port 10 for the passage of blood. Unlike FIG. 1, however, the filtering medium consists of a relatively large surface area (>135 cm²) single, folded filter medium 12 of about 20-40 micron (μ) pore size (or mesh size, as used herein). The filter 12 is folded in accordion fashion to reduce product size while providing a relatively large surface area. In an actual commercial embodiment, the accordion pleats are separated by a similarity folded and relatively large mesh separation screen (not shown) having a pore or mesh size of about 1,000 microns. The screen is present to separate the filter 12 pleats, typically at a distance of about 1 mm wide, and, for practical purposes, that separator screen does not act as a filter. The pleats of the filter are typically about 1.5 cm deep. Even though the single filter of FIG. 2 provides a larger surface area, thus overcoming the small surface area problems of the FIG. 1 filter (e.g. relatively quick occlusion of the filter 4a upper surface), the narrow, vertical channels about 1.5 cm deep tend to fill with clots and microaggregates as illustrated by 6a.

The prior art microaggregate filters of FIGS. 1 and 2 have rigid (non-flexible) housings 14a and 14b and also do not include a blood drip monitor (or "drip chamber") which would permit monitoring of the filtration and infusion rate of blood within the filter. Typically, such drip chambers are added down stream of the filter as part of a blood administration set. In use, both prior art filters wet with blood from the top down. The rigid housings do not permit priming or air bubble removal by simple squeezing (as with a flexible housing). To remove air bubbles, the filters must be inverted to prime them and remove the air by rising through the outlet ports 10. Thus, even if a drip meter were built into the top of such filters, it would be lost during the inverting to prime the filters and remove air bubbles.

Filters of this disclosure are illustrated by FIGS. 3-7.

FIG. 3 is a cross section illustration showing very generally how blood flows in the filter of this invention. FIG. 3 shows a housing 16 made from a flexible, preferably transparent material such as plasticized PVC. Housing 16 has inlet 18 and outlet 20 ports. Incoming blood flows to an inner pre-filter 24 of about 150μ mesh within an outer concentric outer microaggregate filter 26 of about 40μ mesh pore size. Such screens can be made from commercially available square mesh, monofilament polyester materials (PeCap ® screen, Tetko, Inc., Elmsford, N.Y.). Between the vertical walls of inner pre-filter 24 and outer microaggregate filter screen 26 is a space 28 of at least about 0.3 cm, preferably about 0.3 cm to 0.6 cm. As blood flows into inner pre-filter 24, clots and aggregates 32 larger than about 150 microns tend to be held back and sediment toward the bottom of the interior of inner pre-filter 24. Blood material smaller than 150 microns flows relatively unobstructed through pre-filter 24 in the direction of the arrows toward microaggregate outer filter 26 which holds back clots and aggregates larger than about 40 microns, depending on the actual pore or mesh size screen of outer filter 26.

Housing 16 is flexible, and it and flexible filters 24 and 26 are squeezable and can be squeezed to prime incoming blood so that any air rises or moves upward. This is facilitated by including at least one, preferably 3 or 4, tiny longitudinal channels 34 of about 1 mm width to allow air in space 28 to pass through 34. The channel(s) should be large enough to allow passage of air. As can be appreciated, the filter of this invention, in use, wets from the bottom up, thus allowing a built in drip chamber (see remaining figures). This is an added advantage since it permits priming without inverting the filter.

The generally cylindrical and concentric filters 24 and 26 are, in effect, nested together and can be held in place in housing 16 by conventional methods such as friction fit (see FIG. 4) or by solvent welding of plastic screen retain structures made from, for example, Acrylonitrile Butadiene Styrene (ABS).

FIG. 4 is a plan view of a preferred microaggregate filter showing the flexible housing 16 holding by tight friction fit around circular plastic structure ring 44 beneath drip tube 22.

FIG. 5 shows an enlarged cross section of Figure taken at lines 5—5 of FIG. 4. The FIG. 5 illustrates details of the inner 26 an outer 24 filter screens attached to and supported by plastic strut members 38 and 36 respectively. In a preferred case only two such longitudinal struts (about 3 mm×3 mm×70 mm) are used to support each cylindrical screen along with plastic circular structures 40, 42 and 44 which can be attached to screens 24 and 26 by conventional bonding techniques. The volume of the inner and outer nested screens 24 and 26 are about 20 cc and 30 cc, respectively.

FIG. 6 shows a cross section taken through lines 6—6 of FIG. 4 and shows that struts 36 an 38 are slightly off set to allow nesting of inner filter screen 26 within outer filter screen 24 while allowing the screens (at least outer screen 24) to be squeezed through flexible housing 16 to remove air that may exist within the filter, especially within space 28.

FIG. 5a is another cross sectional view of the filter showing how a relatively large volume clots and aggregates 32 can accumulate by sedimentation to the bottom of inner pre-filter 26 without adversely affecting continuous flow of blood as shown by the arrows.

FIG. 7 is an exploded view of the two filters showing how notches 46 and 48 can be provided to assure a controlled offset of supporting struts 36 and 38 that allows both nesting and priming squeezability of outer filter 24. The figure also shows how simple groove 34 is positioned on inner circular support 44a.

FIG. 8 compares our filter with a prior art filter as to time needed to filter a given volume of blood having a normal range hematocrit of 64 at a 36" head.

Given the above disclosures, it is thought that numerous variations will be apparent to those skilled in the art. Accordingly, it is intended that the invention disclosed here should be limited only by the following claims.

We claim:

1. A microaggregate blood filtering system comprising a flexible, filter housing having inlet and outlet ports and an interior containing two generally elongated concentric filtering screens, an inner pre-filter screen and an outer microaggregate filter screen, the inner pre-filter screen having an average pore size of about 150 microns and being adapted to receive blood from the inlet port and adapted to hold back blood aggregates larger than about 150 microns without substantially interfering with the passage of smaller micro aggregates through the inner filter, and the outer filter screen having an average pore size of about 40 microns and being adapted to hold back blood microaggregates larger than about 40 microns without substantially interfering with the passage of smaller aggregates through the outer filter and the outlet port.

2. The system of claim 1 wherein the inner filter screen includes an internal elongated volume, a portion of which is adapted to entrap blood aggregates larger than about 150 microns so that the remaining volume is defined by filter screen which permits the unobstructed passage of smaller aggregates through the screen.

3. The system of claim 1 wherein there is a space of at least about 0.3 cm between the screens.

4. The system of claim 1 wherein the housing includes a space of at least about 0.6 cm between the interior walls of the housing and the exterior walls of the outer screen.

5. The system of claim 3 wherein there is at least one air passageway between the volume occupied by the space between the screens and the inlet port.

6. The system of claim 1 wherein the upper portion of the housing includes a drip chamber and drip tube.

7. In a blood filtering system comprising a housing containing at least two different concentric filtering screens having different pore size openings, an outer screen and an inner blood microaggregate screen, each having a given filtering surface area and defining given larger and smaller volumes, the improvement comprising controlling inner volume, inner surface area of the outer filter screen and the inner surface area of the inner filter screen such that the system has a critical factor, as defined in the specification, ranging from about 1.2 to about 1.5.

8. The system of claim 7 wherein the critical factor is about 1.34.

9. The system of claim 7 wherein the upper portion of the housing includes a drip chamber and drip tube.

10. A method of filtering blood for administration comprising the steps of obtaining a red blood cell preparation and passing it through the filter system of claim 1.

11. The method of claim 10 which comprises passing at least five units of blood through the filter system.

12. The method of claim 10 which includes the additional and subsequent step of infusing the red blood cell preparation into a patient.

* * * * *